(12) United States Patent
Pappas

(10) Patent No.: US 6,206,926 B1
(45) Date of Patent: Mar. 27, 2001

(54) PROSTHETIC KNEE JOINT WITH ENHANCED POSTERIOR STABILIZATION AND DISLOCATION PREVENTION FEATURES

(75) Inventor: Michael J. Pappas, Caldwell, NJ (US)

(73) Assignee: Biomedical Engineering Trust I, NJ (US)

( * ) Notice: Subject to any disclaimer, the term of this patent is extended or adjusted under 35 U.S.C. 154(b) by 0 days.

(21) Appl. No.: 09/191,601

(22) Filed: Nov. 13, 1998

Related U.S. Application Data

(63) Continuation-in-part of application No. 09/165,770, filed on Oct. 2, 1998, now abandoned, which is a continuation-in-part of application No. 08/944,288, filed on Oct. 6, 1997, now abandoned
(60) Provisional application No. 60/065,680, filed on Nov. 18, 1997.

(51) Int. Cl.⁷ ..................................................... A61F 2/38
(52) U.S. Cl. .................................... 623/20.27; 623/20.29; 623/20.33
(58) Field of Search ........................... 623/18, 20, 20.24, 623/20.25, 20.26, 20.27, 20.28

(56) References Cited

U.S. PATENT DOCUMENTS

| | | | |
|---|---|---|---|
| 4,216,549 | * | 8/1980 | Hillberry et al. ................ 623/20.27 |
| 4,224,697 | * | 9/1980 | Murray et al. .......................... 623/20 |
| 5,011,496 | * | 4/1991 | Forte et al. ............................. 623/20 |
| 5,123,928 | * | 6/1992 | Moser ...................................... 623/20 |
| 5,330,534 | * | 7/1994 | Herrington et al. .................... 623/20 |
| 5,395,401 | * | 3/1995 | Bahler ..................................... 623/20 |
| 5,413,607 | * | 5/1995 | Engelbrecht et al. ............ 623/20.26 |

* cited by examiner

*Primary Examiner*—Bruce Snow
(74) *Attorney, Agent, or Firm*—Anthony J. Casella; Gerald E. Hespos; Michael J. Porcoc

(57) ABSTRACT

The prosthetic knee joint is provided for resisting valgus-varus movements. The joint includes a femoral component having a superior bone engaging surface and an inferior bearing surface. A posterior notch extends anteriorly into the posterior end of the femoral component. The prosthetic knee joint further includes a tibial component having an inferior bone engaging surface and a superior bearing surface. A plastic bearing is disposed between the femoral and tibial components. An inferior surface of the plastic bearing is in bearing engagement with the superior surface of the tibial component. A superior bearing surface of the plastic bearing is in articular bearing engagement with the bearing surface of the femoral component. The bearing includes a post projecting proximally from the superior surface. The post is slidably received in the posterior notch of the femoral component and resists valgus-varus moments imposed upon the joint. The post may include medial and lateral cam projections spaced from the superior bearing surface of the bearing. The femoral component may include flanges at the posterior notch for engagement between the cam projections and the superior bearing surface to substantially prevent dislocation.

8 Claims, 8 Drawing Sheets

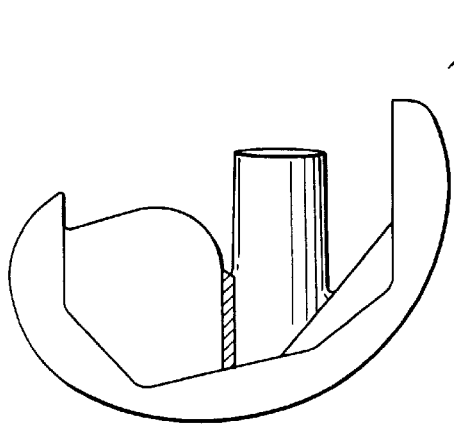
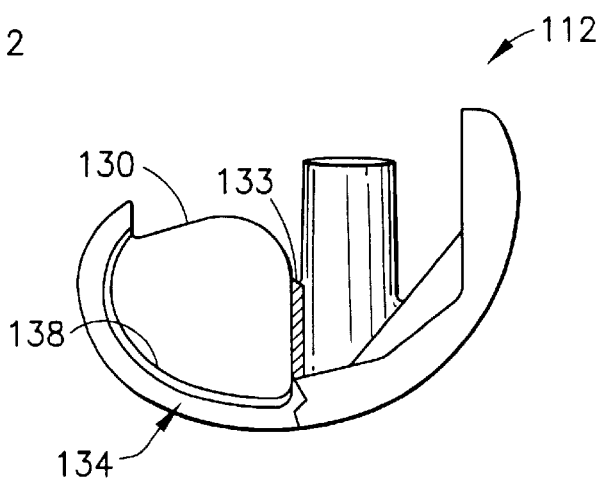
FIG.19    FIG.20
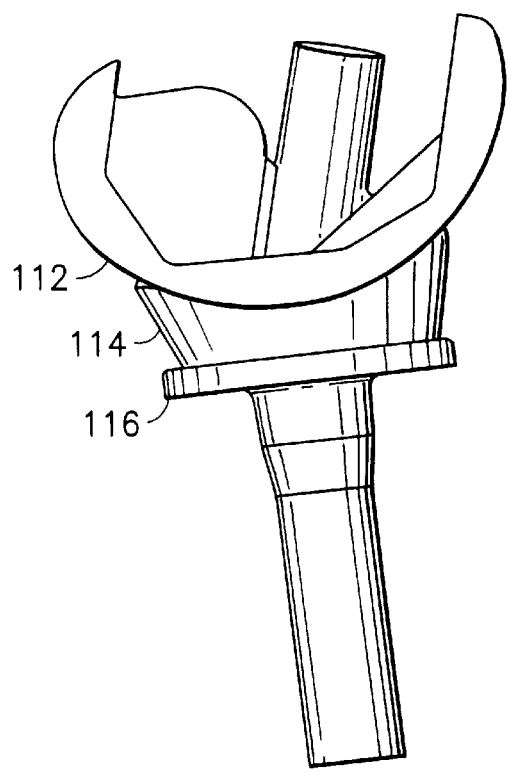
FIG.21

FULL EXTENSION

45° FLEXION

90° FLEXION

120° FLEXION

PROSTHETIC KNEE JOINT WITH ENHANCED POSTERIOR STABILIZATION AND DISLOCATION PREVENTION FEATURES

This application is a continuation-in-part of application Ser. No. 09/165,770 filed Oct. 2, 1998, now abandoned, which in turn is a continuation-in-part of application Ser. No. 08/944,288 filed Oct. 6, 1997, now abandoned. This application also claims the benefit of Provisional Appl. No. 60/065,680 filed Nov. 18, 1997.

BACKGROUND OF THE INVENTION

1. Field of the Invention

The subject invention relates to a knee joint prosthesis having enhanced valgus-varus stability.

2. Description of the Prior Art

A natural knee joint includes the distal end of the femur, the proximal end of the tibia and a meniscus bearing therebetween. The femur and the tibia are held in proper relationship to one another and to the bearing by a plurality of ligaments, including the posterior cruciate ligament, the anterior cruciate ligament and collateral ligaments. Flexion of the knee joint causes the tibia to rotate relative to the femur about an axis extending generally in a medial-to-lateral direction. Flexion also generates rotation of the tibia about its own axis.

Damage or disease can affect the ability of the natural knee to function properly. The damage or disease can deteriorate the bones, the articular cartilage, the ligaments or some combination thereof. A damaged or diseased natural knee can be replaced by a prosthetic knee joint. A prior art knee joint prosthesis includes a femoral component securely mounted to the distal end of a resected femur, a tibial component securely mounted to the proximal end of a resected tibia and a bearing disposed between the femoral and tibial components. The inferior face of the femoral component includes a pair of condyles. The condyles have a convexly arcuate shape, and the superior surface of the bearing has a pair of arcuate concave regions for articular bearing engagement with the condyles of the femoral component. The superior face of the tibial component may be substantially planar and is in bearing engagement with the inferior face of the bearing.

Currently available prosthetic knee joints take many different forms depending upon the preferences of the orthopedic surgeon, the condition of the natural knee and the health, age and mobility of the patient. Some prior art knee joint prostheses fixedly mount the inferior surface of the bearing to the superior surface of the tibial component. Other knee joint prostheses permit rotary movement and/or sliding movement between the bearing and the tibial component. Movement of the bearing against the tibial component achieves many functional advantages described in the prior art. These functional advantages include an avoidance of dislocation in response to normal walking movement without reliance upon a fixed hinged connection. Very effective prior art knee joint prostheses that incorporate certain of the structural features referred to herein are disclosed in U.S. Pat. Nos. 4,470,158 and 4,309,778.

Valgus is a Latin term which translates roughly as bow-legged or knock-kneed. Varus also is a Latin word and translates roughly as crooked. The Latin word varus often is used to define an abnormal position of a bone of the leg or foot. Valgus-varus stability of a knee joint refers to the ability of the joint to resist lateral forces or rotary forces that would tend to urge one knee toward or away from the other. In a knee joint prosthesis, lateral forces or rotary moments that would tend to urge one knee toward or away from the other will also tend to create a dislocation particularly on one side of the prosthesis or the other, as shown, for example, in the prior art prosthesis of FIG. 14.

During normal activities, and with the prosthetic knee joint under compressive loading, the valgus-varus moments are resisted primarily and adequately by the articulating surfaces and ligaments. However, there may be certain instances, for example where ligaments are deficient, when additional valgus-varus stability may be desired.

Some prior art prosthetic knee joints have improved valgus-varus stability by providing a stabilizing post that extends into the posterior region between the femoral condyles that would be occupied by the posterior cruciate ligament if the posterior cruciate ligament were present. For example, U.S. Pat. No. 5,395,401 to Bahler shows a prosthetic knee having a tibial platform and a bearing slidably disposed on the tibial platform. The inferior surface of the bearing is provided with a dove-tailed groove that extends substantially in an anterior-posterior direction and at a location between the two concave condyles formed on the superior surface of the bearing. The bearing shown in U.S. Pat. No. 5,395,401 further includes a notch extending into the posterior side of the bearing at a location between the two concave condyles of the bearing. Thus, the notch registers with the dove-tailed groove of the bearing. The prosthesis of U.S. Pat. No. 5,395,401 further includes a control arm. The control arm includes a post that is pivotally engaged in a recess of the tibial component. The control arm also includes a dove-tailed portion that slidably engages in the dove-tailed groove on the inferior surface of the bearing. Furthermore, the control arm of U.S. Pat. No. 5,395,401 include a post that extends through the notch in the bearing and between the condyles of the femoral component. The post is dimensioned to slidably engage surfaces of the femoral component between the two convex condyles of the femoral component. Thus, the post of the control arm will resist bending moments created by medial or lateral forces, and hence will provide enhanced valgus-varus stability.

Other prior art prosthetic components have provided enhanced valgus-varus stability with posts that extend unitarily from the bearing and into the space between the femoral condyles. Examples of such prior art prosthetic knees are shown, for example, in U.S. Pat. Nos. 5,658,342; 5,489,311; 5,330,534; 4,950,298; 4,888,021, 4,634,444 and 4,568,348. All of these prior art prosthesis are used for joint replacements where the posterior cruciate ligament cannot be retained or are deficient. Additionally, most of these prior art prosthesis are used where both collateral ligaments can be retained. The retained collateral ligaments cooperate with the post to resist valgus-varus moments and to prevent dislocation. Prior art prosthetic joints that have a post extending into the posterior notch between the femoral condyles have not been constructed to both resist valgus-varus moments and to substantially prevent dislocation in instances where only one collateral ligament can be retained.

Accordingly, it is an object of the subject invention to provide a prosthetic knee joint having an enhanced valgus-varus stability.

It is a further object of the subject invention to provide enhanced valgus-varus stability in a prosthetic knee joint without requiring a hinged connection.

It is an additional object of the subject invention to provide a prosthetic knee joint with enhanced protection against dislocation without requiring a hinged connection.

It is yet another object of the subject invention to provide axial rotation without a control arm, and thereby simplifying the design of the prosthetic knee.

SUMMARY OF THE INVENTION

The subject invention is directed to a knee joint prosthesis having a femoral component, a tibial component and a bearing between the femoral and tibial components. The bearing is in rotary and/or sliding bearing engagement with the tibial component and is in articulating bearing engagement with the femoral component. The bearing and the tibial component may include means for limiting rotational and/or sliding movement therebetween. For example a post may project upwardly from the anterior portion of the superior surface of the tibial component, and may be engaged in a groove on the inferior face of the bearing. The dimensions of the groove control the amount of rotary movement.

Posterior regions of the femoral component of the prosthetic joint include a notch between the medial and lateral condyles thereof.

To resist valgus-varus moments, the bearing of the subject prosthetic joint includes a post extending proximally from a posterior region on the superior surface of the bearing and into at least a portion of the notch between the condyles of the femoral component. The post permits articular bearing movement between the femoral component and the bearing. However, the post provides resistance to lateral forces and/or valgus-varus moments, and thereby resists dislocation between the femoral component and the bearing in response to such forces and moments. The post may provide a close sliding engagement with the notch of the femoral component. However, the post preferably is somewhat narrower than the notch to provide a small amount of medial-lateral play between the bearing and the femoral component.

The notch extending into the posterior face of the femoral component does not include a rear restricting surface comparable to the aperture through the femoral component of the prior art fixed bearing prosthesis. However, the prosthesis of the subject invention does provide adequate resistance to posterior dislocation. In particular, the prior art fixed bearing prosthesis with an aperture through the femoral component necessarily includes a relatively flat superior surface on the bearing to accommodate relative rotation of the bearing about the tibial axis and relative to the femur. However, rotation between the bearing and the femur about the tibial axis is not necessary in the subject prosthesis, in view of the rotatable engagement of the bearing on the tibial component. Consequently, the superior surface of the bearing can be more deeply concave and more nearly congruent with the bearing faces of the femoral condyles. This more congruent configuration of the femoral condyles and the superior surface of the bearing combined with the greater concavity of the superior surface of the bearing substantially avoids the need for a complete aperture through the femoral component and an associated posterior wall for engaging and restricting the movement of the bearing in a posterior direction. Greater congruency also provides lower contact stress between the respective components.

The post of the bearing may be formed to include medial and lateral cam projections at locations on the post spaced from the superior concave bearing face. Thus portions of the post furthest from the superior concave bearing face of the bearing may define a greater medial-lateral width. These cam projections define convex inferior faces on the post. The posterior notch in the femoral component may include flanges substantially at the inferior extreme of the posterior notch. The flanges may have convex inferior surfaces that generally conform to the convex shape of the condyles of the femoral component. The flanges further include concave superior faces that may be dimensioned and configured to mate with the convex inferior face formed by the cam projections on the post. More particularly, the flanges of the femoral component will be disposed inferiorly from the cam projections of the post and superiorly of the superior bearing surfaces on the bearing. As a result, dislocation of the femoral component away from the bearing is substantially controlled and/or prevented.

BRIEF DESCRIPTION OF THE DRAWINGS

FIG. 19 is a side elevational view of the femoral component shown in FIGS. 17 and 18.

FIG. 20 is a side elevational view, partly in section of the femoral component shown in FIG. 19.

FIG. 21 is a side elevational view showing the femoral component assembled onto the bearing and tibial components depicted in FIGS. 15–20.

DETAILED DESCRIPTION OF THE PREFERRED EMBODIMENTS

Figure 1:
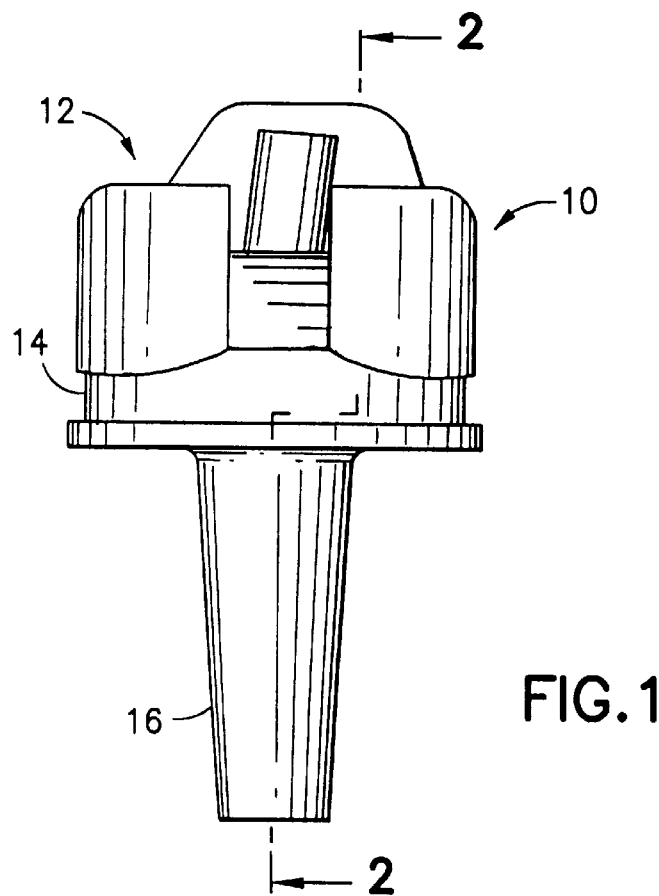
FIG. 1 is a rear elevational view of the subject prosthesis and showing reaction to valgus-varus moments.

The prosthetic joint of the subject invention is identified generally by the numeral 10 in FIGS. 1–4. The prosthetic joint 10 includes a femoral component 12, a bearing 14 and a tibial component 16.

Figure 5:
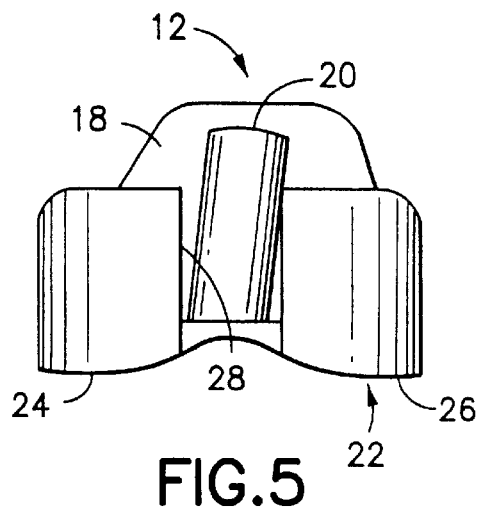
FIG. 5 is a front elevational view of the femoral component of the subject prosthesis.
Figure 6:
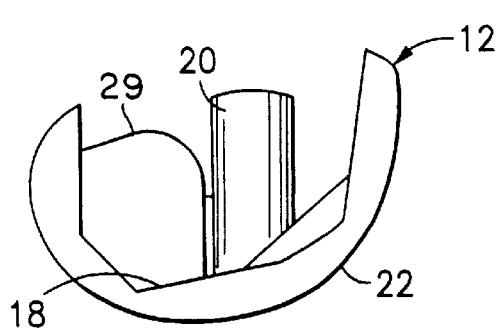
FIG. 6 is a side elevational view of the femoral component.
Figure 7:
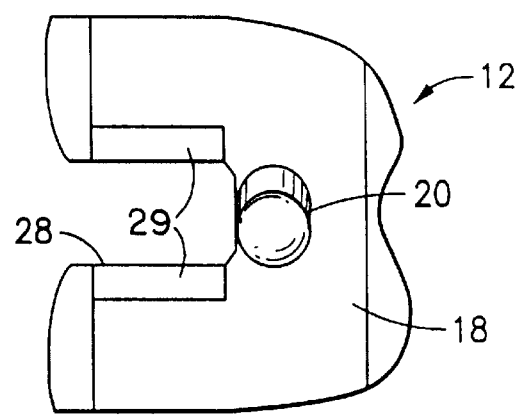
FIG. 7 is a top plan view of the femoral component.

With reference to FIGS. 5–7, the femoral component 12 includes a superior mounting face 18 for mounting to the resected distal end of the femur. The mounting face 18 includes mounting post 20 for secure attachment to a modular stem (not shown), which in turn is engaged in a cavity drilled axially into the resected distal end of the femur. The femoral component 12 further includes an inferior bearing face identified generally by the numeral 22. As shown most clearly in FIG. 5, the bearing face 22 of the femoral component 12 includes a pair of condyles 24 and 26, each of which are highly polished. The femoral component 12 is further characterized by a posterior notch 28 extending anteriorly from the posterior extreme of the femoral component 12 substantially to the mounting post 20. The notch 28 is partly defined by parallel medial and lateral walls 29.

Figure 8:
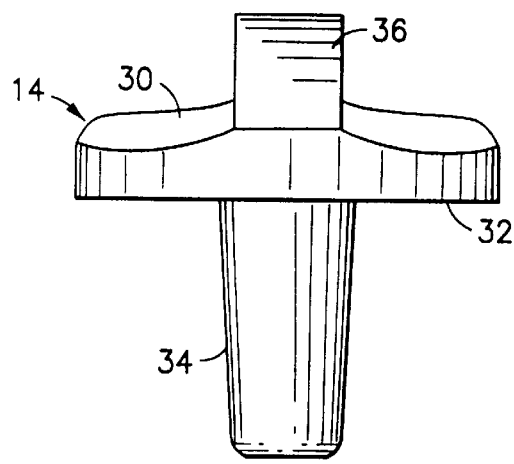
FIG. 8 is a front elevational view of the bearing of the subject prosthesis.
Figure 9:
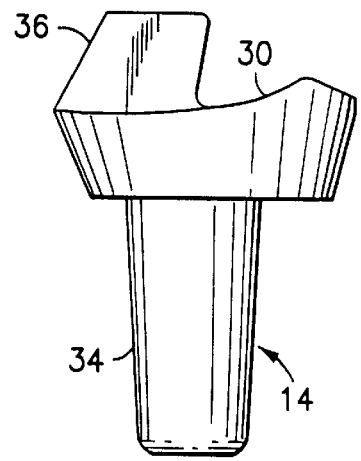
FIG. 9 is a side elevational view of the bearing.
Figure 10:
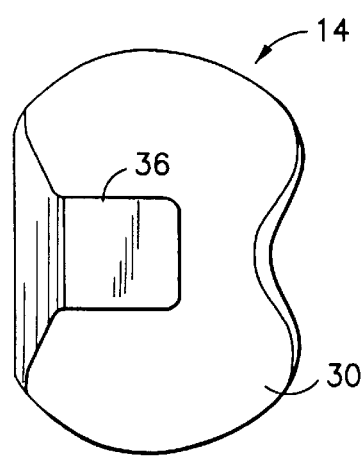
FIG. 10 is a top plan view of the bearing.

The bearing 14, as shown most clearly in FIGS. 8–10, includes a superior bearing surface 30 for articular bearing engagement with the inferior bearing face 22 of the femoral component 12. The superior bearing surface 30 is defined by a pair of concave bearing regions. As shown most clearly in FIGS. 2 and 3, the shapes defined by the two concave regions of the superior bearing surface 30 are substantially congruent with portions of the convex shape defined by the condyles 24 and 26 which form the bearing face 22 of the femoral component 12. As explained further herein, this congruency provides posterior stabilization and substantially prevents posterior dislocation. The bearing 14 further includes a substantially planar inferior bearing surface 32 for rotary bearing engagement against the tibial component 16 as explained herein. A conical projection 34 extends from the inferior bearing surface 32 for rotary bearing engagement in a correspondingly configured cavity in the tibial component 16.

The bearing 14 is further characterized by a post 36 projecting proximally from posterior regions of the concave superior bearing surface. The post 36 has parallel planar medial and lateral faces and is dimensioned for close sliding engagement in the posterior notch 28 of the femoral component 12.

Figure 11:
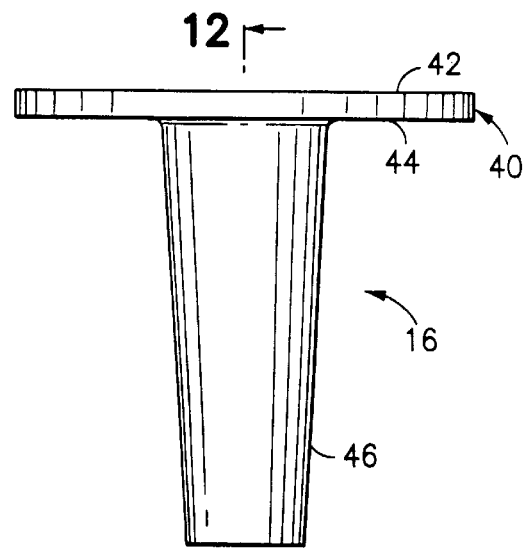
FIG. 11 is a front elevational view of a tibial component in accordance with the subject invention.
Figure 12:
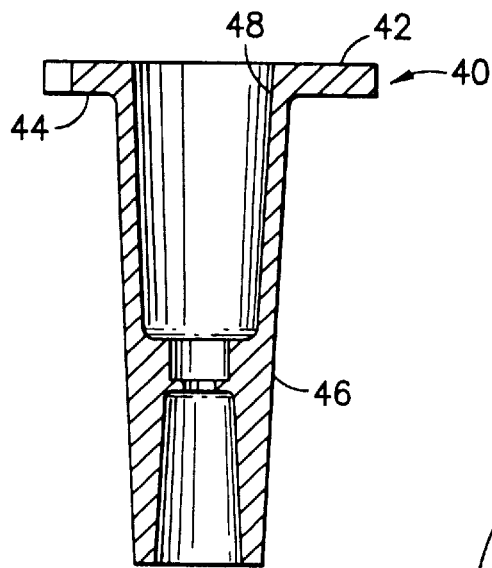
FIG. 12 is a cross-sectional view of the tibial component taken along line 12—12 in FIG. 11.
Figure 13:
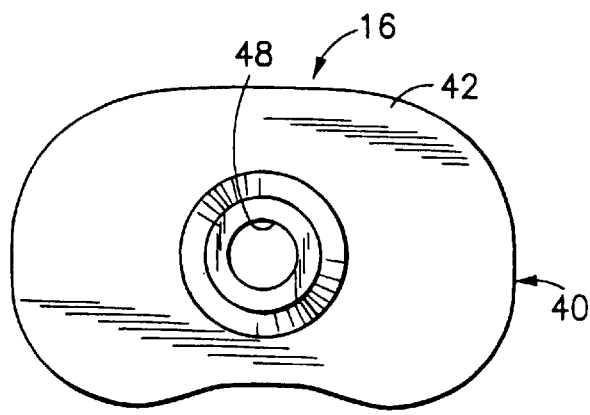
FIG. 13 is a top plan view of the tibial component.
Figure 14:
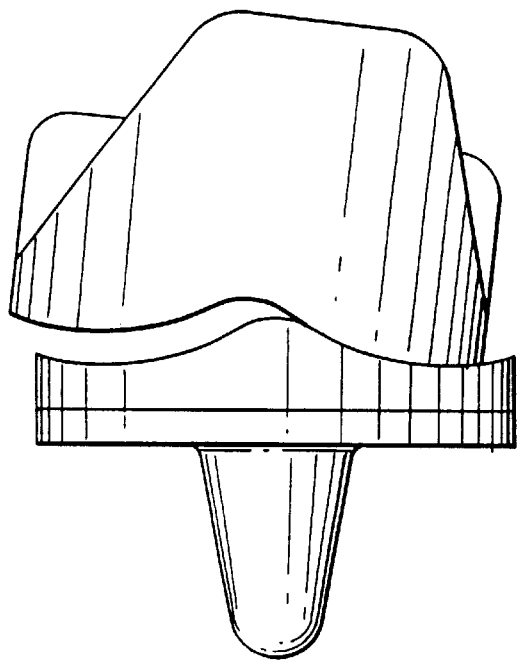
FIG. 14 is a front elevational view of a prior art prothesis showing the prior art reaction to valgus-varus moments.

With reference to FIGS. 11–13, the tibial component 16 includes a bearing platform 40 having a superior planar bearing face 42 and an opposed inferior mounting face 44. A mounting post 46 projects distally from the inferior face 44 for engagement in the cavity drilled into the proximal end of the resected tibia. The superior bearing face 42 of the tibial platform 40 includes a cavity 48 extending axially into the mounting post 46. The cavity 48 is dimensioned to rotatably receive the conical projection 34 of the bearing 14.

Figure 2:
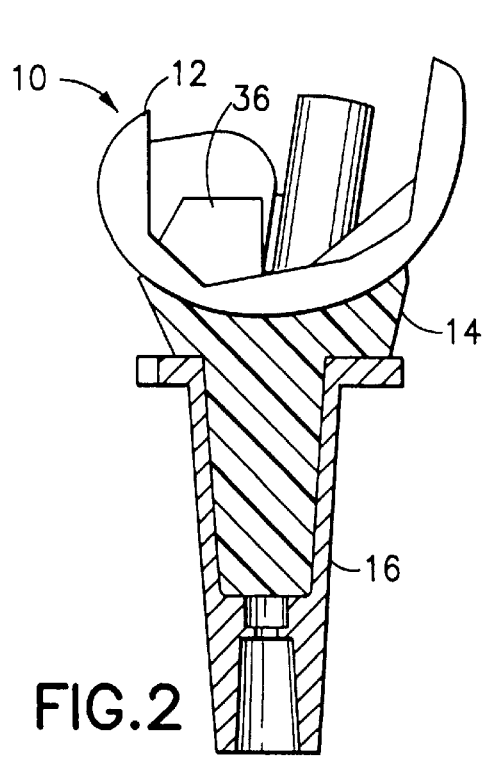
FIG. 2 is a cross-sectional view taken along line 2—2 in FIG. 1 and with a wall removed to show the bearing post.
Figure 3:
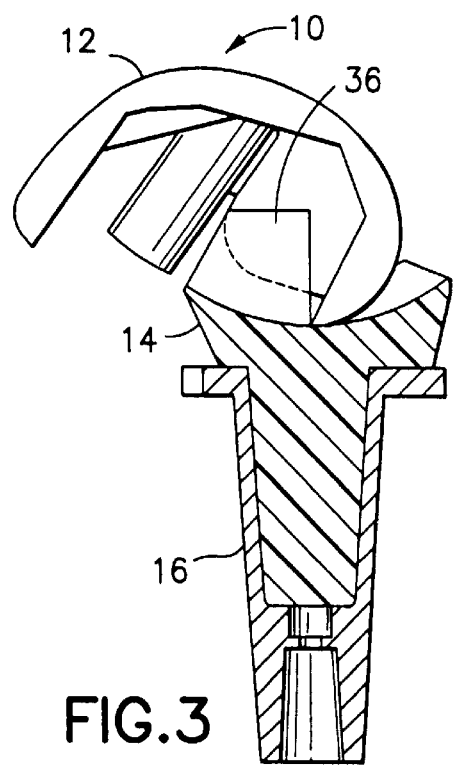
FIG. 3 is a side elevational view similar to FIG. 2, but showing the prosthesis at 150° flexion.
Figure 4:
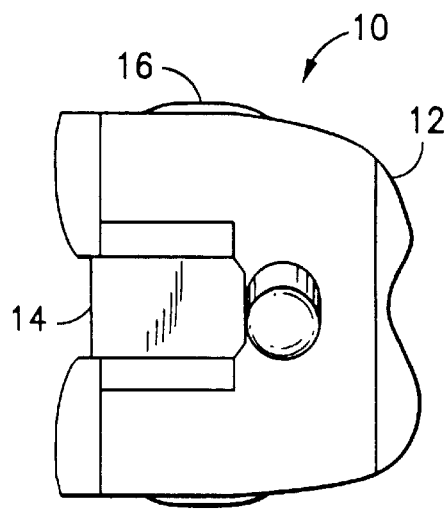
FIG. 4 is a top plan view of the prosthesis shown in FIG. 3.

The components of the prosthesis 10 are assembled as shown in FIGS. 1–4. In the assembled condition, the conical projection 34 of the bearing 14 is rotatably engaged in the conical cavity 48 of the tibial component 16, and the inferior face 32 of the bearing 14 is in rotary bearing relationship with the superior face 42 of the tibial component 16. The inferior bearing surface 22 of the femoral component 12 is in articular bearing engagement with the concave superior surface 30 of the bearing 14. Additionally, the condyles 24 and 26 that define the inferior bearing surface 22 of the femoral component 12 are substantially congruent with the concave superior bearing surface 30 of the bearing 14 as shown in FIGS. 2 and 3 and as described above for certain flexion ranges (i.e., up through 45° flexion). At greater ranges of flexion, theoretical line contact will exist between the femoral component 12 and the bearing 14.

The post 36 of the bearing 14 is slidably received in the posterior notch 28 of the femoral component 12 to resist valgus-varus moments imposed upon the prosthetic component. As shown in FIGS. 2 and 3, the engagement of the post 36 in the notch 28 is effective for resisting valgus-varus moments for virtually all ranges of movement of the prosthetic component. The substantial congruency of the superior bearing face 32 of the bearing 14 with the condyles 24 and 26 of the inferior bearing face 22 of the femoral component 12 through certain ranges of movement substantially ensures posterior stabilization despite the fully opened posterior end of the notch 28 in the femoral component 12. Thus, valgus-varus stabilization is provided without adversely affecting mobility, and specifically while providing rotation of the bearing on the tibial component.

Figure 18:
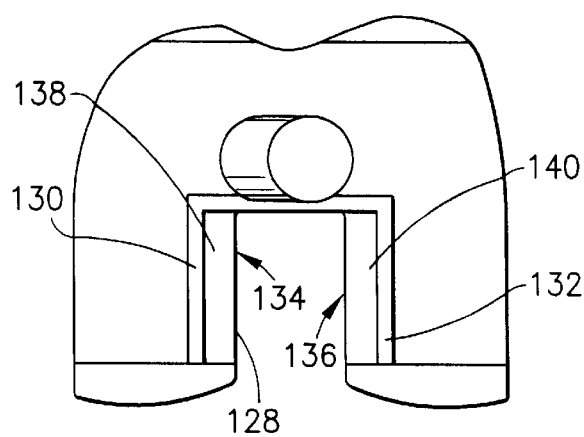
FIG. 18 is a top plan view of the femoral component of FIG. 17.

An alternate prosthetic joint 110 is illustrated in FIGS. 15–28. The alternate prosthetic joint 110 includes a femoral component 112, a bearing 114 and a tibial component 116. The tibial component 116 is virtually identical to the tibial component 16 described above and illustrated in FIGS. 11–13. The femoral component 112, also bears considerable similarities to the femoral component 12 described and illustrated above. More particularly, the femoral component 112 preferably is formed from a titanium alloy with a titanium nitride coating. The femoral component includes a post 120 for secure attachment to a modular extension 121. As shown most clearly in FIG. 22, the modular extension 121 is securely engaged in a cavity drilled axially into the resected distal end of the femur 900. The femoral component 112 further includes an inferior bearing face 122 having a pair of convex condyles 124 and 126 which are highly polished. The femoral component 112 further is characterized by a posterior notch 128 extending from the posterior extreme of the femoral component 112 substantially to the mounting post 120. In the previous embodiment, the notch was defined by parallel medial and lateral walls, and the medial-lateral distance between the walls was constant at any position therealong. In the subject embodiment, the notch 128 is partly defined by a pair of parallel walls 130 and 132 and an anterior wall 133. However, a pair of flanges 134 and 136 project toward one another from portions of the walls 130 and 132 substantially at the inferior bearing surfaces of the condyles 124 and 126 of the femoral component 112. Thus, the distance between the walls 130 and 132 defining the posterior notch 128 is smallest at the flanges 134 and 136 and is larger at more superior positions in the notch 128. The flanges 134 and 136 are characterized by cavity cam surfaces 138 and 140 which face generally in a superior direction as illustrated most clearly in FIG. 18.

The bearing 114 also is similar to the bearing 14 described and illustrated above. In particular, the bearing 114 preferably is formed from a UHMWPe and includes a superior bearing surface 142 defined by a pair of concave bearing regions 144 and 146. The bearing 114 includes a post 148 that projects proximally or superiorly from a posterior portion of the concave superior surfaces 142 between the concave bearing regions 144 and 146. In the previous embodiment, the post was of constant medial-lateral width at all locations thereon, and thus included two parallel side surfaces. In the embodiment of FIGS. 15–28, the post 148 includes cam projections 150 and 152 on opposite medial and lateral sides of the post 148 at locations spaced from the superior bearing surface 142. Thus, the post 148 includes a minor width "w" at more inferior positions thereon and a major width "W" at superior positions thereon. The minor width "w" is slightly less than the distance between the flanges 134 and 136 in the posterior notch 128 of the femoral component 112. The major width "W" at superior locations on the post 148 is greater than the distance between the flanges 134 and 136 in the notch 128 of the femoral component 112, but is slightly less than the width of the posterior notch 128 at other locations between the walls 130 and 132 of the femoral component 112 that define the notch 128. As shown most clearly in FIG. 16, the cam projections 150 and 152 have convex inferior surfaces 154 and 156.

Implantation is illustrated with reference to FIG. 22. More particularly, the tibial platform 116 is implanted into the tibia 500 as in the prior art, and the bearing 114 is assembled onto the tibial platform 116. The knee 600 then is flexed to about 120° of flexion, and the modular extension 121 of the femoral component 112 is inserted into the cavity prepared in the femur 900. As the femoral component 112 is moved into position on the resected distal end of the femur 900, the superior cavity cam surfaces 138 and 140 of the flanges 134 and 136 clear the inferior cam surfaces 154 and 156 on the cam projections 150 and 152 of the post 148 of the bearing 114 and allow full seating of the femoral component 112 onto the femur 900 as shown in FIG. 23. The posterior distal region 901 of the femur 900 must have a relief 902, as shown in FIG. 23, to clear the posterior surface on the post 148 of the bearing 114 to provide full flexion needed to implant the femoral component 112.

Figures 22, 23:
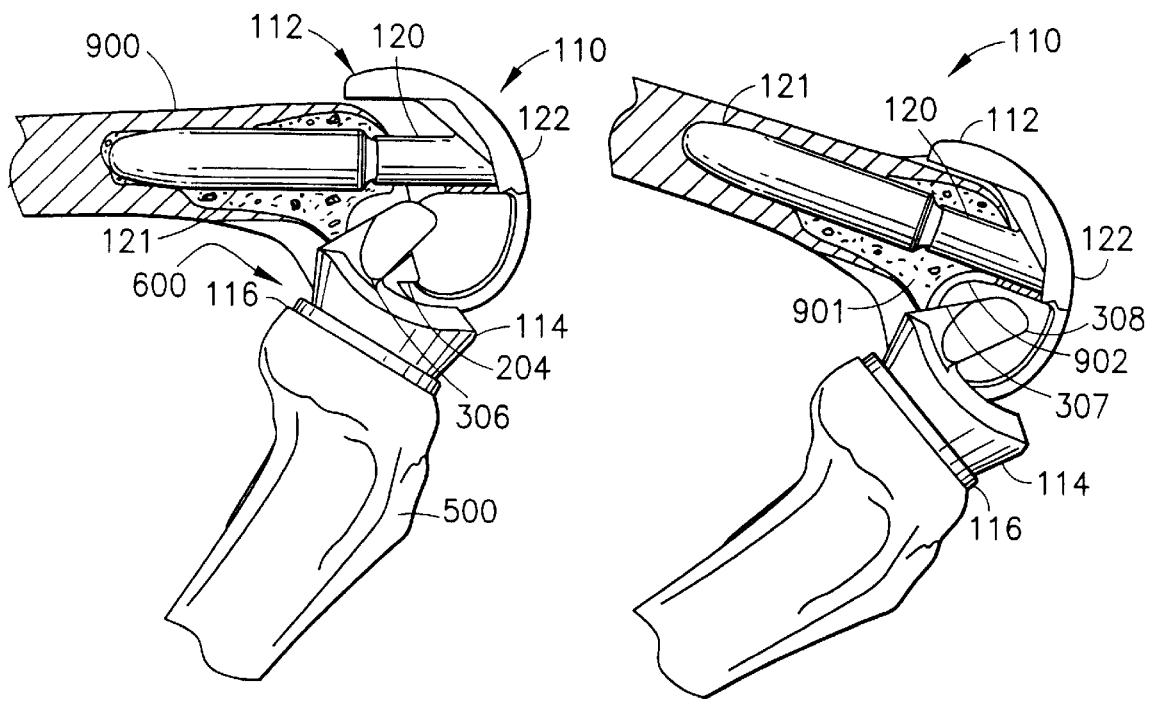
FIG. 22 is a cross-sectional view of a knee during implantation of the prosthesis shown in FIGS. 15–21.
FIG. 23 is a cross-sectional view similar to FIG. 22, showing the knee after implantation of the prosthesis, and indicating resistance to dislocation.
Figure 26:
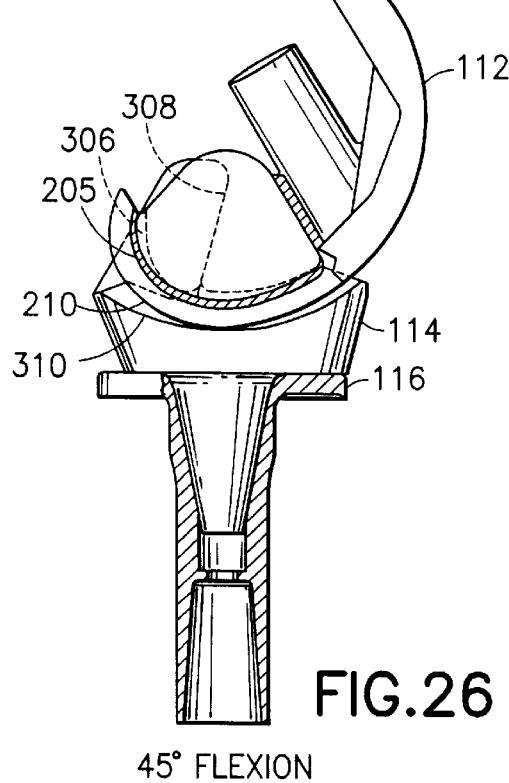

As illustrated in FIG. 23, the tibia 500 cannot be dislocated posteriorly since the presence of the posterior distal region 901 inhibits posterior tibial motion by impingement with the posterior surface of the post 148. As shown in FIG. 26, the cam cavity surface 138 and 140 on the flanges 134 and 136 and the anterior regions of the cam projections 150 and 152 prevent anterior dislocation of the tibia. The outer side surface of the cam projections 150 and 152 of the post engage the cavity side walls 130 and 132 to prevent medial-lateral dislocation. Thus, the bearing 114 is trapped in the femoral component 112 and cannot be dislocated.

Figure 15:
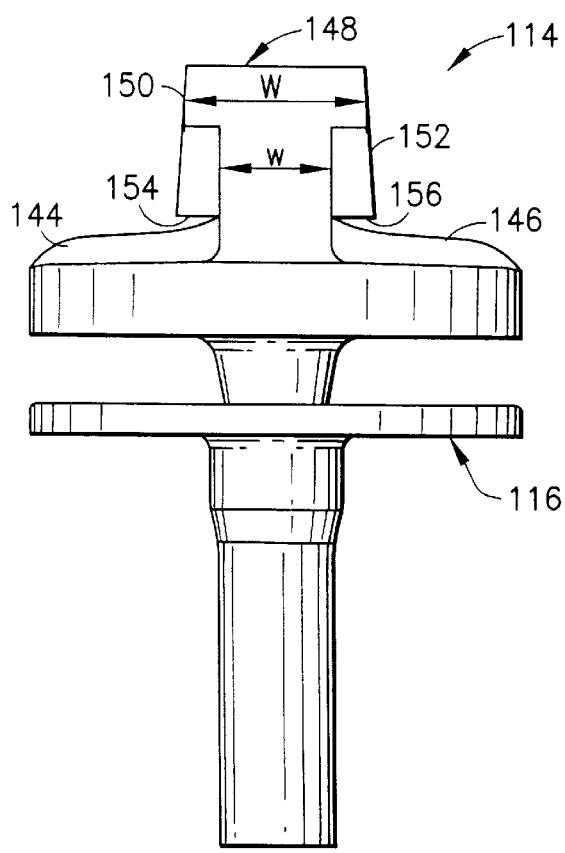
FIG. 15 is an exploded front elevational view of the tibial component depicted in FIGS. 1–3, 11 and 12 used with an alternate bearing.
Figure 16:
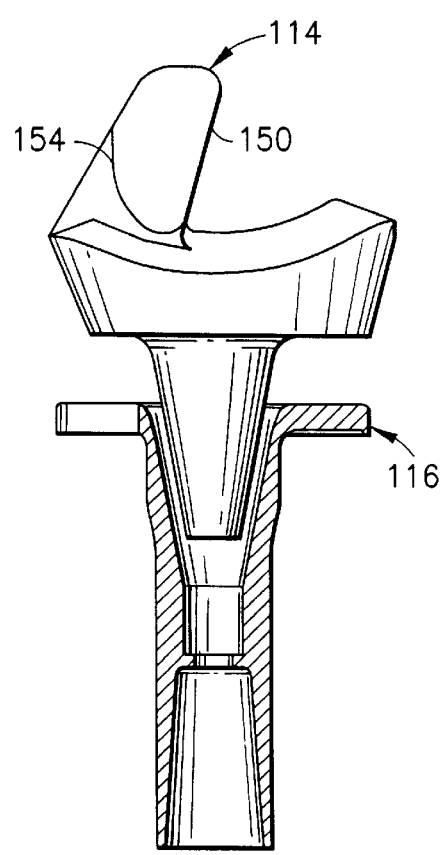
FIG. 16 is an exploded side elevational view of the assembly depicted in FIG. 15.
Figure 17:
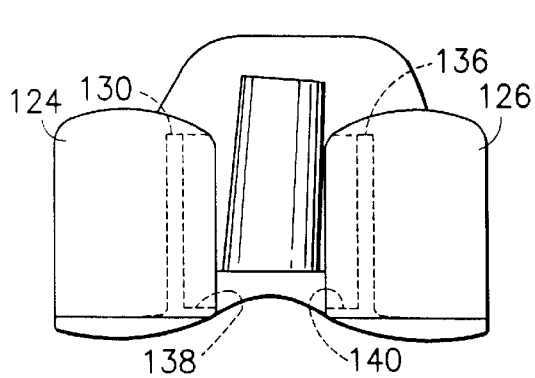
FIG. 17 is a front elevational view of an alternate femoral component for use with the bearing depicted in FIGS. 15 and 16.
Figure 24:
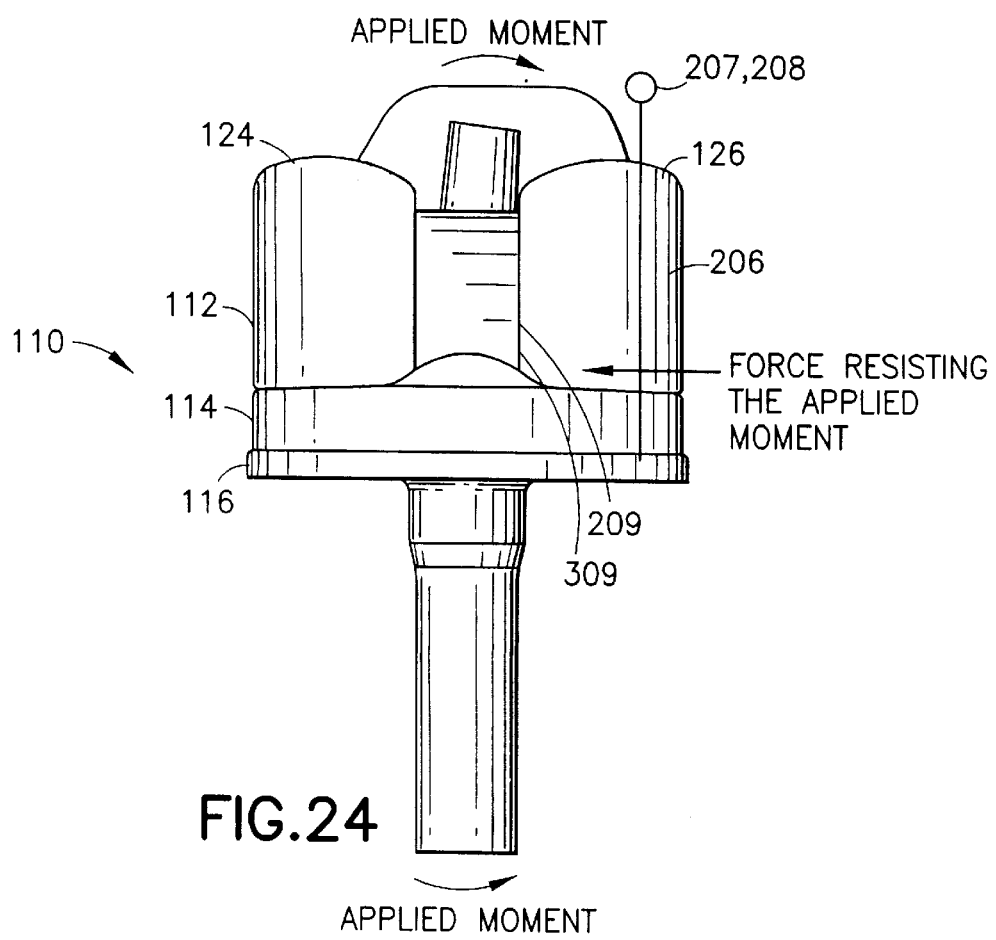
FIG. 24 is a schematic front elevational view of the assembled prosthesis illustrating force vectors applied to the joint during use.

There are two means of valgus-varus stability. With reference to FIG. 24, and under load bearing conditions, the normal compressive load will press the femoral condyles 124 and 126 against the matching articular concave bearing regions 144 and 146. The match is such that under compression, any rotation of the femoral component 112, in the plane of FIG. 24, must be around an axis 207 and through the center of curvature 208 of the femoral condyle 206. Rotation about the axis 207 produces impingement between an inferior aspect of either the flange 134 or 136 at the notch 128 in a femoral condyle 124 or 126 and a side surface of the post 148 below the cam projections 150 and 152. This contact produces a reaction force resisting any valgus-varus moment applied to the joint. Thus, bending of the post 148 need not occur to resist the applied moment. The outer side walls of the post 145, as shown in FIG. 15 may be tapered to prevent such bending during load bearing.

During non-load bearing phases, any valgus-varus moment is small, but the post may be subject to small bending loads, since joint compression may not occur. The post must be strong enough in bending to resist such moments.

Figure 25:
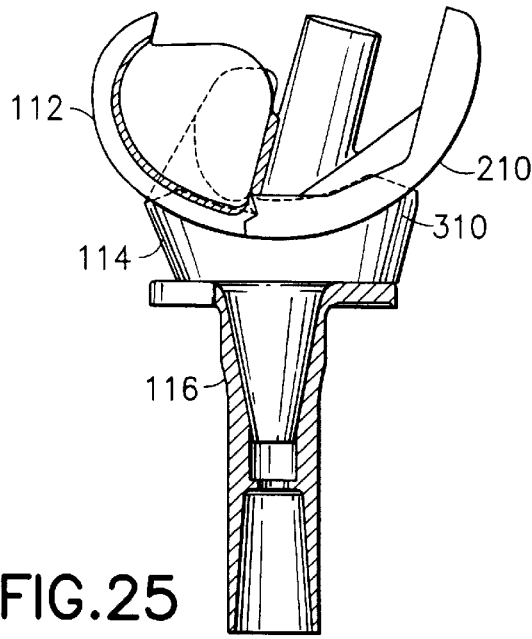
FIGS. 25–28 are cross-sectional views of the assembled prosthesis at different degrees of flexion.
Figure 27:
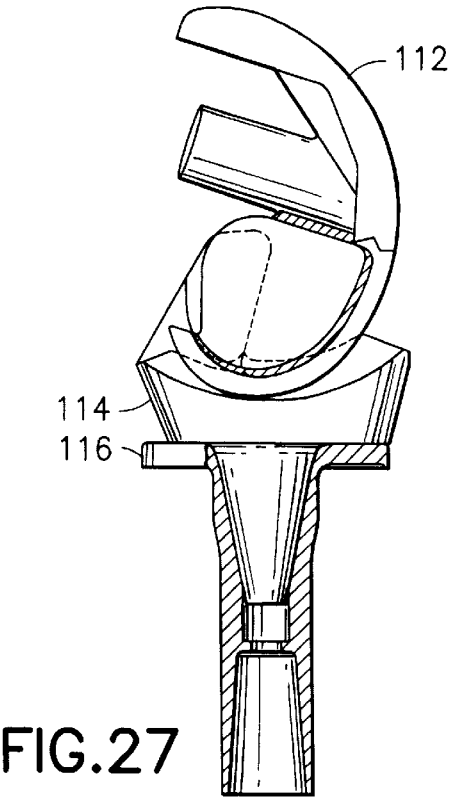
Figure 28:
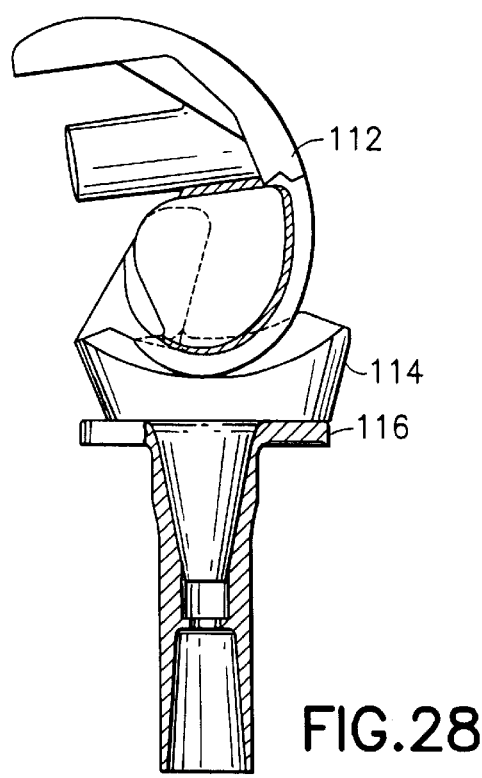

Cooperative action of the cavity and post cam surfaces respectively are illustrated in FIGS. 25–28. In these figures, the bearing 114 is drawn so as it is "seen through", to better illustrate this cooperation. In the full extension, as illustrated in FIG. 25, the cam surfaces are not in contact. They act only to prevent A-P dislocation in the absence of load bearing. Under load bearing, the shape of the inferior femoral articular bearing face 122 pressing against the superior bearing surface 142 provides stability and position. As flexion progresses, the concave superior cavity cam surfaces 138 and 140 will engage the convex inferior cam surfaces 154 and 156 of the cam projections 150 and 152 on the post 148, as shown in FIGS. 26 and 27, and will force the femoral component 112 posteriorly with respect to the bearing 114. This posterior movement, or femoral roll back, improves quadriceps effectiveness. The roll back is present for any normal load bearing activity likely to be performed by a knee replacement patient. This posterior movement may be lost at full flexion, as shown in FIG. 28, but this is unimportant, since load bearing normally does not occur in this motion phase, or at least occurs very infrequently.

While the invention has been described with respect to a preferred embodiment, it is apparent that various changes can be made without departing from the scope of the invention as defined by the appended claims.

What is claimed is:

1. A knee joint prosthesis comprising:
   a femoral component having a superior surface configured for mounting to a femur, an inferior articular bearing surface which includes medial and lateral convex condyles, a posterior notch extending anteriorly into a posterior face of the femoral component, and continuously between the superior and inferior surfaces, said notch being defined by substantially parallel spaced apart medial and lateral walls projecting in a superior direction from the superior surface and by medial and lateral flanges projecting toward one another from locations on the respective medial and lateral walls adjacent the inferior articular bearing surface of the femoral component, said flanges of said femoral component having inferior surfaces substantially conforming to shapes defined by said convex condyles, said flanges further having arcuately concave superior bearing faces;
   a tibial component; and
   a bearing disposed between the femoral and tibial components, the bearing having a superior bearing face in articular bearing engagement with the inferior articular bearing surface of the femoral component, said bearing further including a post projecting from the superior face thereof and slidably disposed in the posterior notch of the femoral component, said post including medial and lateral cam projections spaced from said superior bearing face of said bearing, said flanges of said femoral component being between the cam projections and the superior bearing face of the bearing, the medial and lateral cam projections of the bearing have arcuately convex inferior bearing surfaces for bearing engagement against the arcuately concave superior bearing surface of the flanges of the femoral component for resisting valgus-varus moments applied to the prosthesis, the arcuately convex inferior bearing surfaces each defining a curvature smaller than the arcuately concave superior bearing surfaces of the flanges to enable relative anterior-posterior movement between the femoral component and the bearing.

2. The prosthesis of claim 1, wherein the flanges of the femoral component are substantially equally spaced from one another at all locations along said notch.

3. The prosthesis of claim 1, wherein the femoral component further comprises an anterior wall extending between the medial and lateral walls and defining a portion of the notch.

4. The prosthesis of claim 1, wherein the bearing is unitarily formed from a UHMWPe.

5. The prosthesis of claim 1, wherein the femoral component and the tibial component both are formed from metallic materials.

6. The prosthesis of claim 5, wherein the femoral and tibial components are formed from a titanium alloy with a titanium nitride coating thereon.

7. The prosthesis of claim 1, wherein the tibial component includes an inferior surface configured for attachment to a resected superior portion of a tibia.

8. The prosthesis of claim 1, wherein the inferior surface of the bearing is movably disposed on the superior surface of the tibial component.

* * * * *